United States Patent
Pedrazzini

(10) Patent No.: US 9,869,687 B2
(45) Date of Patent: Jan. 16, 2018

(54) APPARATUS FOR AUTOMATICALLY DEPOSITING, PRESERVING AND RECOVERING SPECIMENS OF BIOLOGICAL MATERIALS IN/FROM A REFRIGERATED STORE USING TWO DISTINCT STATIC ROBOTS

(71) Applicant: Inpeco Holding Ltd., Qormi (MT)

(72) Inventor: Gianandrea Pedrazzini, Paradiso (CH)

(73) Assignee: INPECO HOLDING LTD., Qormi (MT)

( * ) Notice: Subject to any disclaimer, the term of this patent is extended or adjusted under 35 U.S.C. 154(b) by 190 days.

(21) Appl. No.: 14/646,208

(22) PCT Filed: Nov. 25, 2013

(86) PCT No.: PCT/EP2013/074534
§ 371 (c)(1),
(2) Date: May 20, 2015

(87) PCT Pub. No.: WO2014/082944
PCT Pub. Date: Jun. 5, 2014

(65) Prior Publication Data
US 2015/0260746 A1 Sep. 17, 2015

(30) Foreign Application Priority Data
Nov. 27, 2012 (IT) .............................. MI2012A2011

(51) Int. Cl.
*G01N 35/04* (2006.01)
*G01N 35/10* (2006.01)
*G01N 35/00* (2006.01)

(52) U.S. Cl.
CPC ..... *G01N 35/1065* (2013.01); *G01N 35/0099* (2013.01); *G01N 35/00584* (2013.01);
(Continued)

(58) Field of Classification Search
CPC ........ B01L 3/5805; B01L 7/525; B65B 21/12; B65B 35/04; F25D 11/02; F25D 13/02;
(Continued)

(56) References Cited

U.S. PATENT DOCUMENTS 3,599,314 A * 8/1971 Harrison .................... B21J 5/00
164/111
6,068,393 A * 5/2000 Hutchins ................ B01J 19/004
422/67
(Continued)

FOREIGN PATENT DOCUMENTS

EP 1 248 170 A1 10/2002
EP 1 477 813 A1 11/2004
(Continued)

*Primary Examiner* — Anna M Momper
*Assistant Examiner* — Brendan P Tighe
(74) *Attorney, Agent, or Firm* — Jacobson Holman, PLLC.

(57) ABSTRACT

There is described an apparatus for automatically depositing, preserving and recovering specimens of biological materials contained in test tubes in/from a refrigerated store. Said apparatus comprises two test tube handling devices between test tube containers and carriers positioned on a conveyor adapted to automatically handle said test tubes; said two test tube handling devices are intended the one to load said test tubes from the refrigerated store to the conveyor and the other to unload test tubes from the conveyor (4) to the refrigerated store. Said test some containers are handled between said refrigerated store and said test tube handling devices by a container handling device.

5 Claims, 14 Drawing Sheets

(52) U.S. Cl.
CPC ......... *G01N 35/04* (2013.01); *G01N 35/1081* (2013.01); *G01N 2035/00435* (2013.01); *G01N 2035/0406* (2013.01); *G01N 2035/0425* (2013.01); *G01N 2035/1051* (2013.01)

(58) Field of Classification Search
CPC ........ F25D 13/04; F25D 23/02; F25D 23/021; F25D 23/123; F25D 25/00; F25D 25/005; F25D 25/02; F25D 25/021; F25D 25/022; F25D 25/028; F25D 25/04; G01N 35/00584; G01N 35/0099; G01N 35/04; G01N 35/1065; G01N 35/1081; G01N 2035/00435; G01N 2035/0406; G01N 2035/0425; G01N 2035/0445; G01N 2035/0462; G01N 2035/1051
USPC ................. 62/265, 266, 374, 378, 382, 441; 294/81.21; 414/225.01, 281
See application file for complete search history.

(56) References Cited

U.S. PATENT DOCUMENTS

| | | |
|---|---|---|
| 2004/0184959 A1 | 9/2004 | Itoh |
| 2005/0013734 A1 | 1/2005 | Vann et al. |
| 2008/0190735 A1* | 8/2008 | Luoma ..................... B01L 9/00 198/340 |
| 2009/0003981 A1 | 1/2009 | Miller |
| 2010/0028214 A1 | 2/2010 | Howard et al. |
| 2010/0303590 A1* | 12/2010 | Pedrazzini ............. G01N 35/04 414/331.02 |
| 2011/0226584 A1 | 9/2011 | Ek |

FOREIGN PATENT DOCUMENTS

| | | |
|---|---|---|
| EP | 2 240 787 A1 | 10/2010 |
| WO | 2009/077465 A1 | 6/2009 |

\* cited by examiner

APPARATUS FOR AUTOMATICALLY DEPOSITING, PRESERVING AND RECOVERING SPECIMENS OF BIOLOGICAL MATERIALS IN/FROM A REFRIGERATED STORE USING TWO DISTINCT STATIC ROBOTS

The present invention relates to an apparatus for automatically depositing, preserving and recovering specimens of biological materials in/from a refrigerated store using two distinct static robots.

BACKGROUND OF THE INVENTION

Nowadays, in specialized laboratories, where tests are carried out on specimens of biological material of patients, the need to prepare refrigerated stores, where the aforesaid specimens can be temporarily stored in a circle along the automated laboratory system, is increasingly felt.

The subject stores must be adapted to ensure adequate preservation of the biological samples contained in test tubes, in anticipation of their future reuse for a subsequent series of tests, possibly even after several days since their collection.

The Applicant has already filed an earlier patent EP 2240787 related to a store which meets the above requirements. Reference shall therefore be made to such a patent for a comprehensive overview of the features of the equipment described therein.

Such a patent, in particular, shows the interfacing of the above store with a portion of a conveyor adapted to the automatic handling of biological material tubes along the entire system, highlighting the possibility of alternatively carrying out the dual task of unloading tubes from the conveyor to the store (for subsequently storing them) and loading tubes from the store to the conveyor (for redirecting the samples, along the conveyor, towards the appropriate testing modules).

Although the above apparatus is able, as mentioned, to carry out both the loading and the unloading operations, the device included therein and adapted to handle the test tubes, both in one direction and in the other, is a single robot able to carry out translational movements in three directions, thus reaching all the points necessary for the execution of the proper tube handling process.

It is understood that the above robot can alternatively handle either a loading or an unloading operation.

US-2005/013734, EP-1477813 and EP-1248170 show apparatuses for handling test tubes to/from a refrigerated store.

BRIEF SUMMARY OF THE INVENTION

Therefore, it is the object of the present invention to provide an apparatus which allows the simultaneous execution of unloading of test tubes from the conveyor to the store and loading of test tubes from the store to the conveyor.

This is in response to the increasingly large number of biological specimens which may need to be handled by an automation system as a whole, and therefore to the need to store or recover from the store with increasing frequency the test tubes containing the specimens themselves.

This and other objects are achieved by an apparatus as described in claim 1.

BRIEF DESCRIPTION OF THE SEVERAL VIEWS OF THE DRAWING(S)

These and other features of the present invention will become more apparent from the following detailed description of an embodiment thereof, made by way of a non-limiting example in the accompanying drawings, in which.

DETAILED DESCRIPTION OF THE INVENTION

Figure 1:
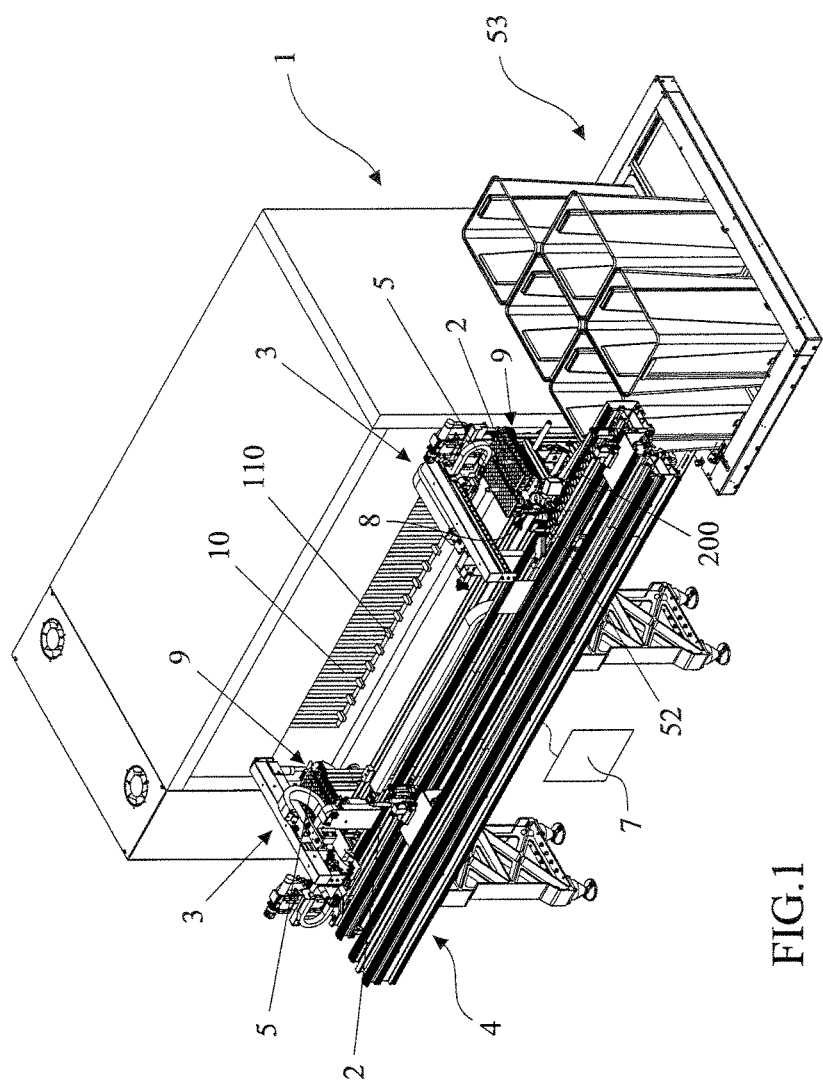
FIG. 1 shows a perspective view of the apparatus according to the invention.

FIG. 1 shows an apparatus for automatically depositing, preserving and recovering specimens of biological materials in a refrigerated store 1 adapted to accommodate and store biological material containers, such as test tubes 2, which are one by one handled by two distinct static robots, i.e. two test tube handling devices 3, between a portion of a test tube conveyor 4 and dedicated containers 5 of a sorted plurality of test tubes (multi-tube containers or "racks").

Figure 2:
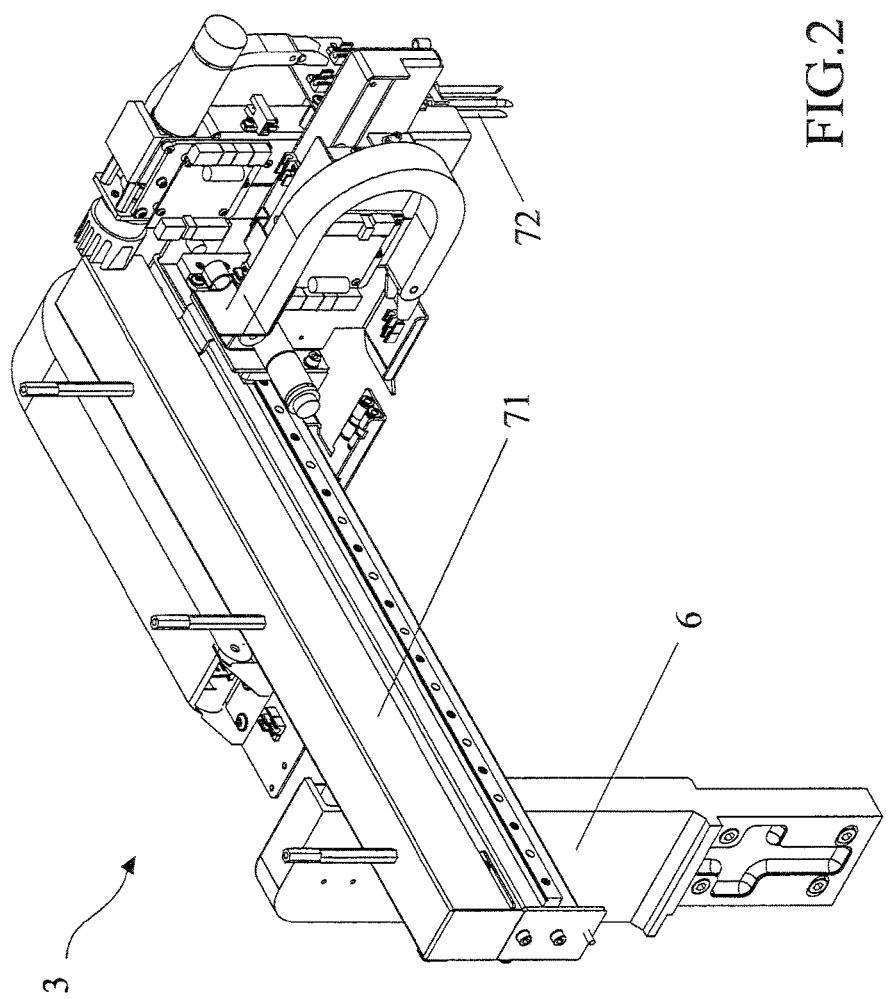
FIG. 2 shows a perspective view of a test tube handling apparatus.

The two test tube handling devices 3 are each attached to a respective support bracket 6 (FIG. 2), at the opposite ends of the interface region between the refrigerated store 1 and the conveyor portion 4, as shown in FIG. 1. Each includes a mechanical arm 71 to which a clamp 72 is connected, adapted to clamp the test tubes 2 during the step of handling them. The mechanical arm 71 is capable of carrying out translating movements in the three dimensions, reaching all the points necessary for the execution of the proper test tube handling process, on the basis of the commands sent by a central control unit 7.

The central control unit 7 (FIG. 1) is a software application provided with a memory which contains all the information needed to perform the appropriate activities on test tubes 2, and adapted to store the life cycle during the process; it also coordinates all the devices involved in the operations of loading/unloading of the test tubes 2.

Figure 3:
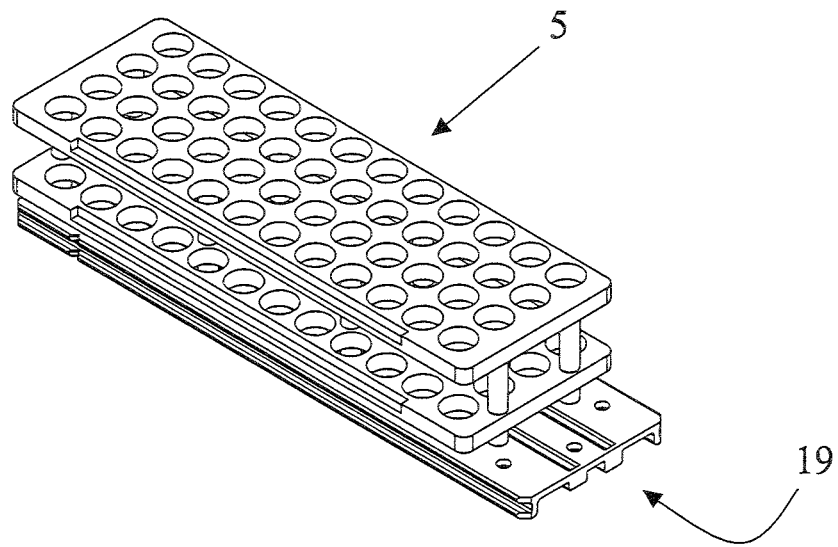
FIG. 3 shows a perspective view of a test tube container.
Figure 4:
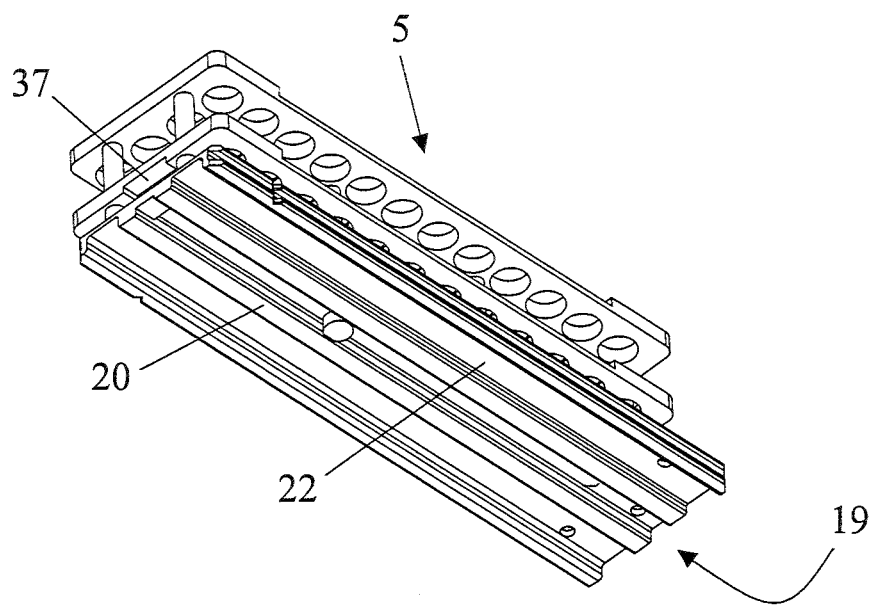
FIG. 4 shows a perspective view of the bottom surface of the test tube container.

The two test tube handling devices 3 deal the one (the rightmost one in FIG. 1) with carrying out the loading operation of test tubes 2, recovered from the refrigerated store 1, on conveyor 4 and the other one (on the left in FIG. 1) with carrying out the opposite operation, i.e. the unloading of test tubes 2 from conveyor 4 towards the refrigerated store 1 for their subsequent storage. The test tubes 2, as mentioned, are picked up or introduced from/into test tube containers 5 (FIGS. 3, 4) which during some steps are carried, one at a time, by a single container handling device 8 (FIGS. 5, 6) for the entire apparatus, while during other steps they are accommodated on revolving plates 9 (FIGS. 7, 8, 9) with two locations, said 9 plates being provided in two units, i.e. one in correspondence with each test tube handling device 3. Since each revolving plate 9 has two locations, it can accommodate up to two test tube containers 5 at the same time.

The refrigerated store 1 is, as regards its internal structure, similar to the one described in the previous patent EP-2240787, in particular as regards the handling mechanism of the various shelves in which the stored test tube containers 5 are positioned, separated by lanes.

Figure 12:
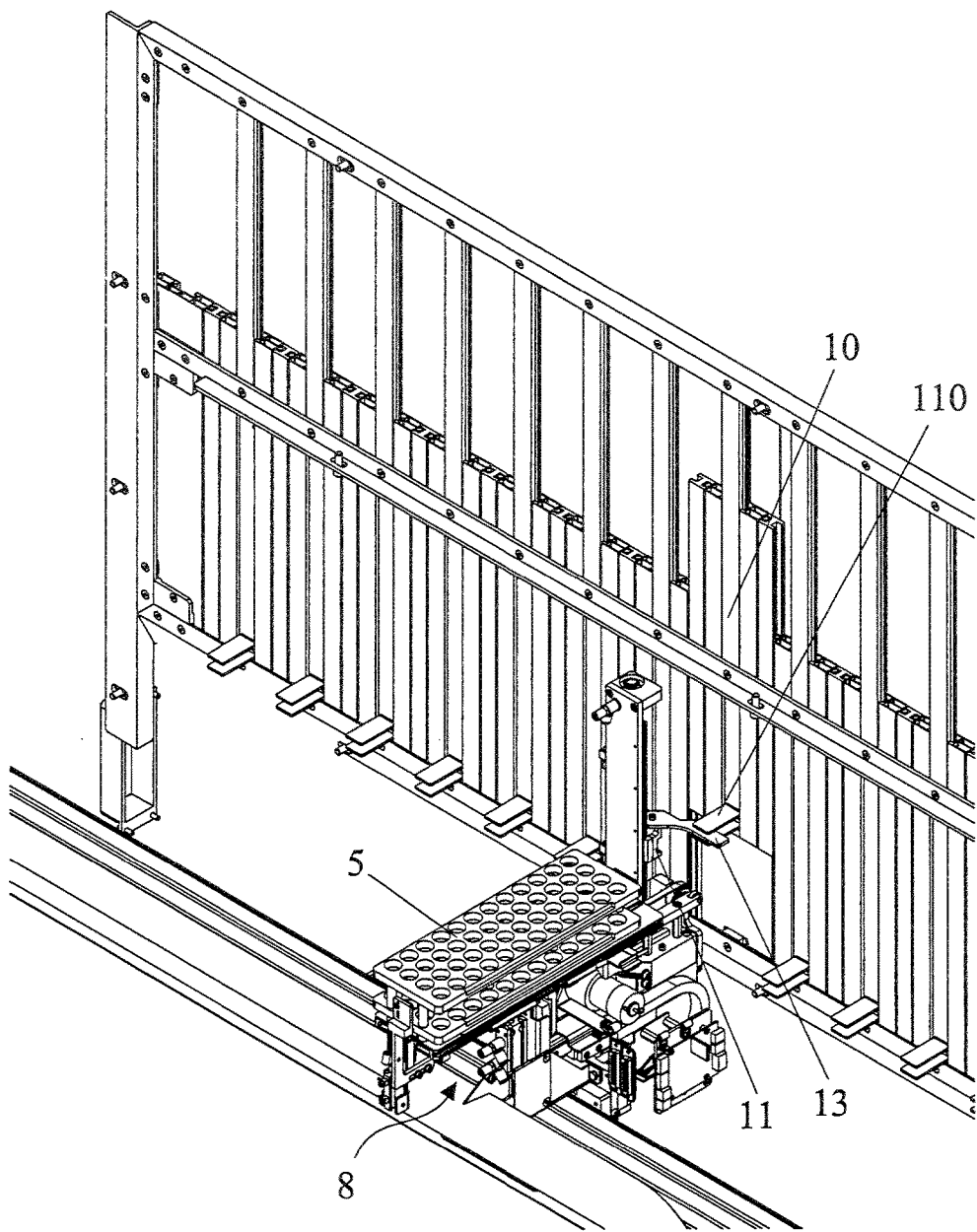
FIG. 12 shows a perspective detail of a handling step of a test tube container between the refrigerated store and the container handling device.
Figure 13:
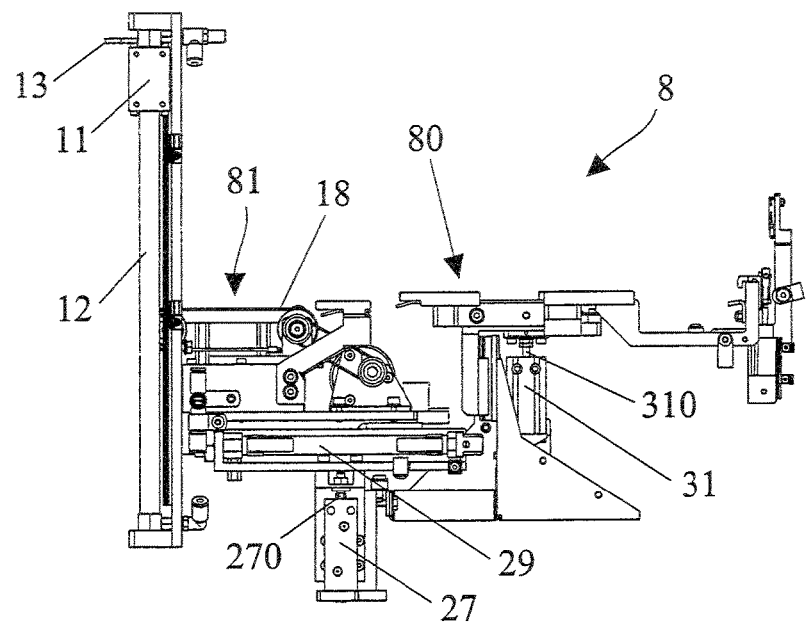
FIGS. 13, 14, 15 and 16 show side views of four different possible configurations of the container handling device.

On the front side, store 1 has sliding doors 10 (FIG. 1), in the vicinity of each lane, such as to ensure only the opening of the sliding door 10 corresponding to the lane involved in the handling operation of the single test tube container 5 (FIG. 12).

Obviously, the sliding door 10 thus opens, through a command sent by the control unit 7, only if a test tube container 5 needs to be moved from the refrigerated store 1 to the container handling device 8 or vice versa; otherwise, all sliding doors 10 remain closed so as to ensure the heat insulation of the refrigerated store 1.

Figure 10:
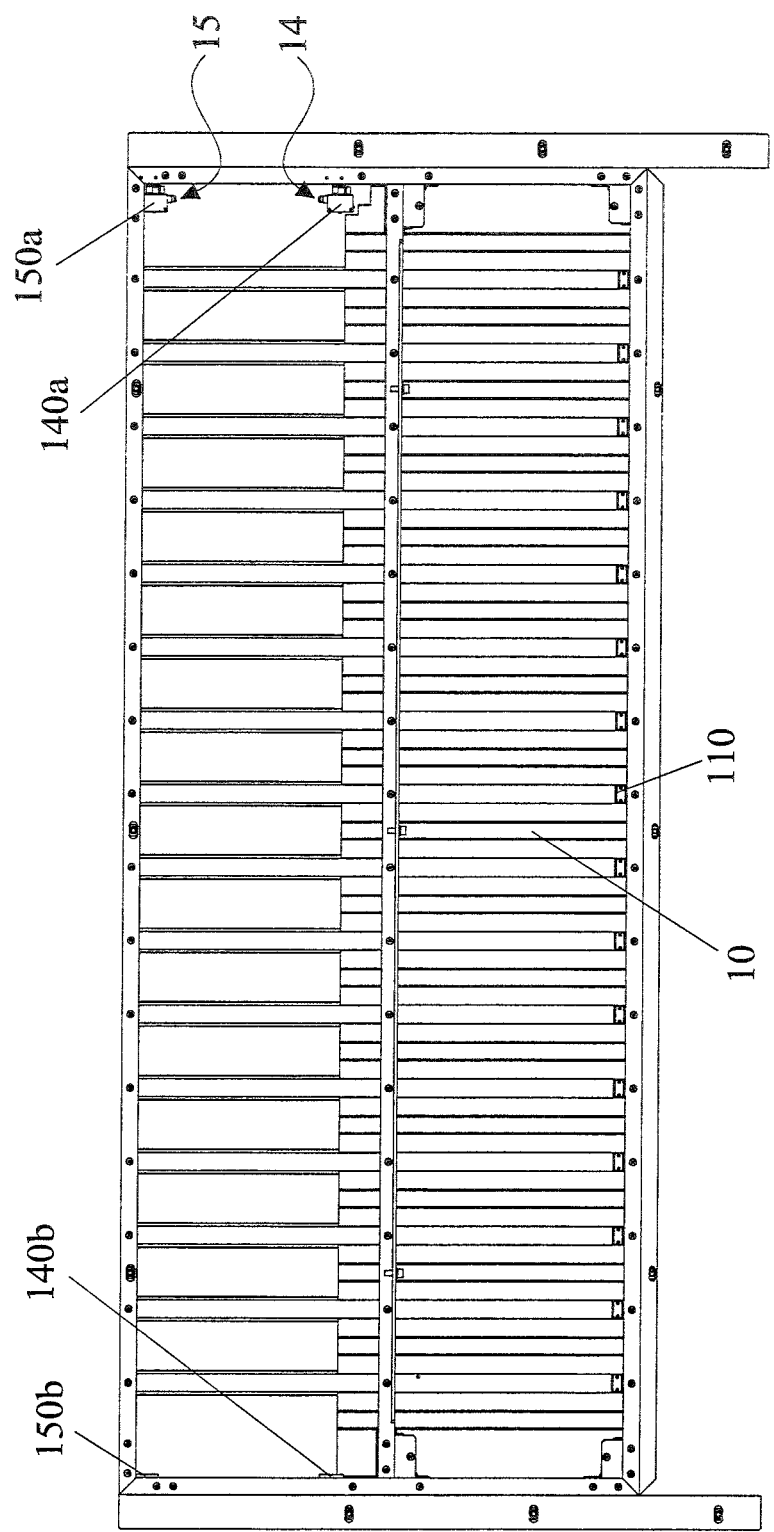
FIG. 10 shows a front view of sliding doors along the front wall of the refrigerated store.

In correspondence with the front wall of the refrigerated store 1, which includes the sliding doors 10, a closed door sensor 14 and a lifted door sensor 15 are secured to a framing (FIG. 10). They both consist of a laser beam emitter 140a, 150a towards a receiver 140b, 150b. The arrival of the laser beam emitted by emitter 140a to receiver 140b recognizes the situation in which all sliding doors 10 are closed. Likewise, the interruption of the laser beam emitted by emitter 150a towards receiver 140b recognizes the situation in which one of the sliding doors 10 is fully lifted.

Figure 11:
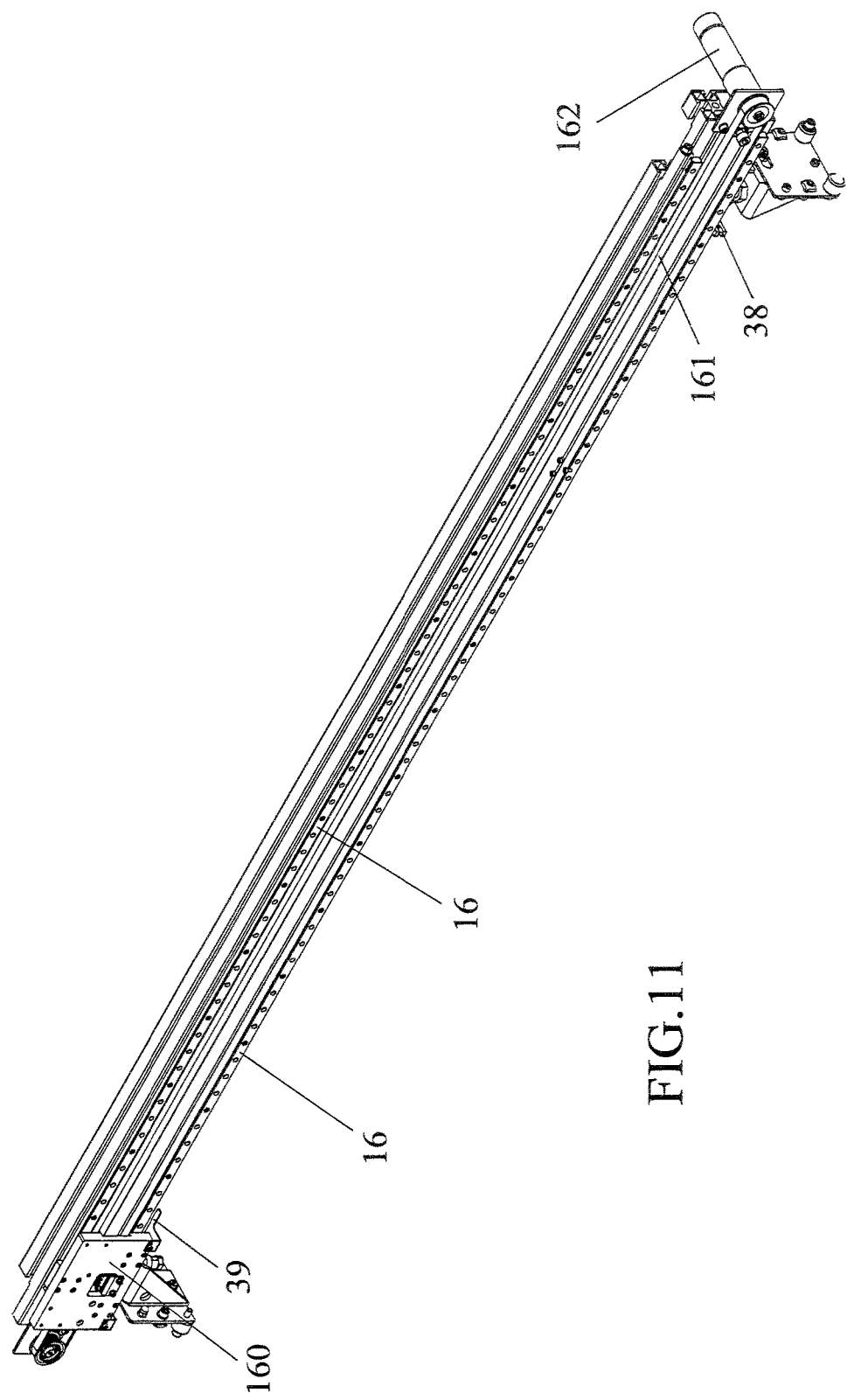
FIG. 11 shows a perspective view of sliding means of the container handling device along the apparatus, having removed the container handling device itself.

The container handling device 8 is intended to move test tube containers 5 from inside to outside the refrigerated store 1 and vice versa, and is able to slide parallel to conveyor 4 by means of a carriage 160, to which device 8 is hooked, which moves along a sliding guide 16 (FIG. 11) mounted on a profile adjacent to conveyor 4. A belt 161 driven by an electrical motor 162 slides on said sliding guide 16; such a sliding allows the container handling device 8 to reach each of the positions corresponding to one of the sliding doors 10.

A sensor 38 is provided in the vicinity of the sliding guide 16 (FIG. 11) adapted to detect the position of the container handling device 8 and, in the specific case, the reaching by the same of the maximum point in its translational movement parallel to conveyor 4, i.e. its arrival in correspondence with the revolving plate 9 on the left (according to the representation in FIG. 1), i.e. the unloading one. Such a detection is possible thanks to the engagement of sensor 38 with a tongue 39 (FIG. 11), integral with carriage 160 and therefore with the container handling device 8, when the container handling device 8 reaches the unloading plate 9.

Only one sensor 38 is required since the handling along the horizontal axis of the container handling device 8, which allows it to be positioned exactly in correspondence with each lane or each sliding door 10, is managed by an encoder of the electric motor 162 which moves the container handling device 8 along the sliding guide 16.

The container handling device 8 comprises a sliding door opening cylinder consisting of a slider 11 (FIGS. 5, 6) sliding along a fixed rod 12; slider 11 is further hooked to a tongue 13. After the horizontal sliding step of device 8 to position itself along the appropriate lane, through the aforementioned movement managed by the encoder of the electrical motor 162, once device 8 has arrived in correspondence with the appropriate lane, the upward pneumatic displacement of slider 11 is controlled: this allows tongue 13, projecting with respect to slider 11, to hook an appendix 110 positioned in correspondence of with sliding door 10 so that also such an appendix 110 is raised, and therewith the gate of sliding door 10, which opens accordingly (FIG. 12).

The container handling device 8 comprises a front block 81, which faces the sliding doors 10 of the refrigerated store 1. Such a front block 81 comprises a support 17 (FIGS. 5, 6) on which a toothed translation track 18 is mounted, which enables the test tube container 5 to slide translating from the refrigerated store 1 to a resting surface 80 on device 8, and vice versa (the test tube container 5 is omitted in FIGS. 5 and 6 to facilitate the display of all the elements of device 8).

The bottom surface 19 (FIGS. 3, 4) of the test tube container 5 is provided with a toothed guide 20 such as to allow the translation of the test tube container 5 on the toothed translation track 18.

Sliding bearings 21 (FIGS. 5, 6) ensure the balance of the test tube container 5 along a guide 22 of container 5 (FIG. 4) during the translation.

Figure 5:
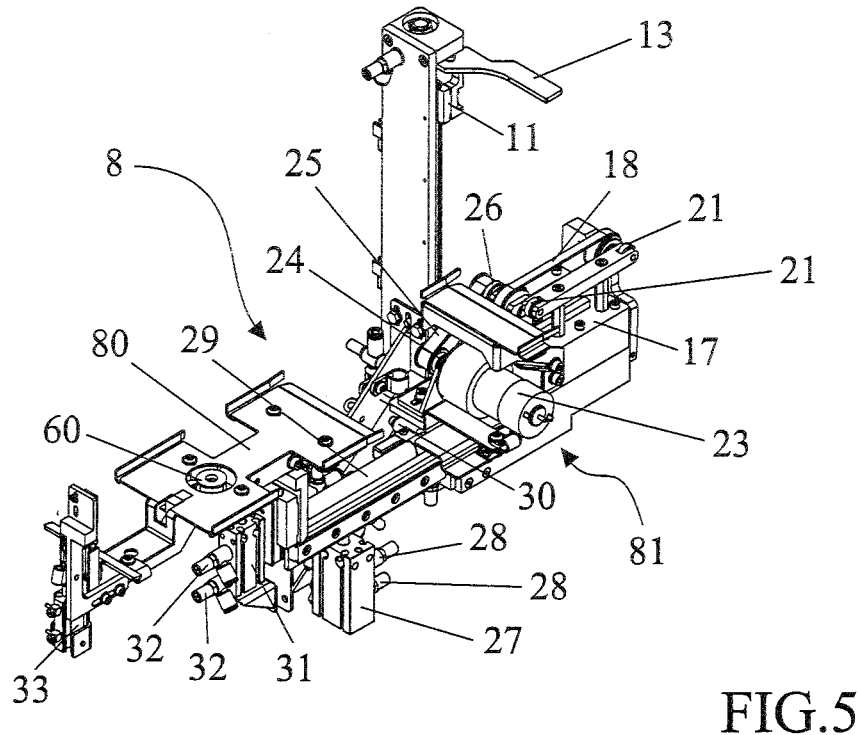
FIG. 5 shows a perspective view of a container handling device.
Figure 6:
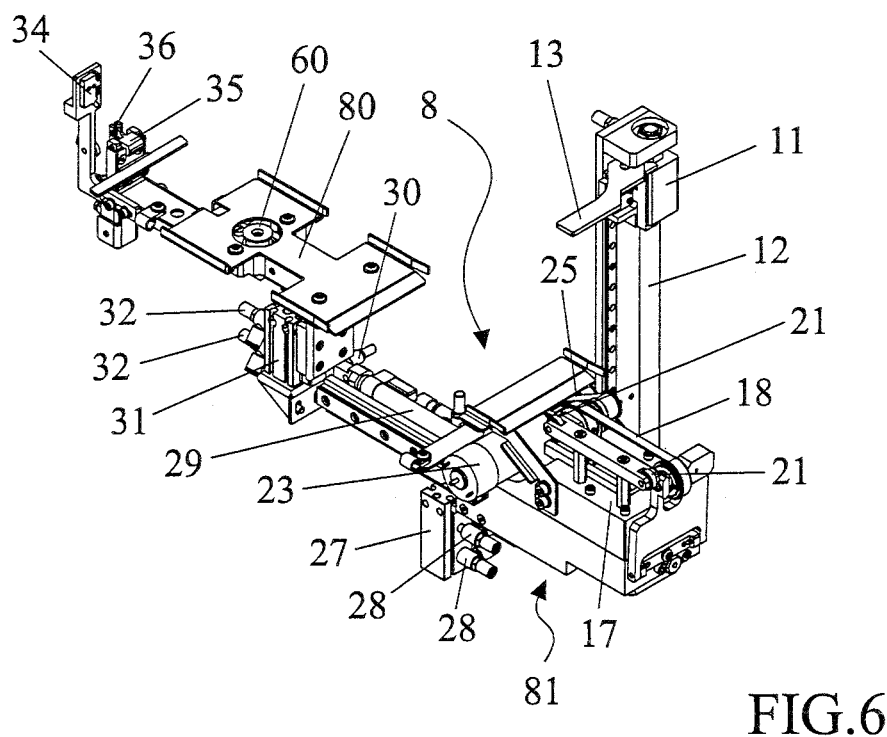
FIG. 6 shows, again, the container handling device, from a perspective rotated by 90° with respect to the previous one.

The movement of the toothed translation track 18 is generated by an electrical motor 23, whose movement is transmitted by a shaft 24 through a belt 25 to a pulley 26 (FIG. 5).

Depending on the various operating steps of the container handling device 8, both the front block 81 and the resting surface 80 thereof can carry out a vertical translation, thus assuming a high or low position, as will be better clarified hereafter. Such vertical translations are ensured by the action of a pneumatic cylinder 27 (and corresponding piston 270) powered by solenoid valves through two flow regulators 28 as regards the front block 81, and by a pneumatic cylinder 31 (and corresponding piston 310) powered by solenoid valves through two flow regulators 32 as regards the resting surface 80 respectively (FIGS. 5, 6, 13-16). Moreover, the container handling device 8 comprises a pneumatic cylinder 29 powered by solenoid valves through two flow regulators 30, which allows the sliding of the test tube container 5 from the lane of the refrigerated store 1 towards the resting surface 80, and vice versa, to be completed (FIGS. 5, 6, 13-16).

Moreover, a test tube container lock cylinder 33 is provided (FIG. 5), actuated by a test tube presence sensor 34 (FIG. 6) adapted to detect the presence of a test tube container 5 on the resting surface 80 of the container handling device 8. When the test tube container 5 translates and is received by the resting surface 80, at the end of such a translation sensor 34 detects it, thus activating the raising of cylinder 33; thereby, a hook 35 (FIG. 6), which is pivoted to a pivot 36, lowers and inserts into a suitable housing 37 (FIG. 4) of the test tube container 5, thus locking it.

As a further confirmation of the presence of a test tube container 5 on the resting surface 80, an antenna 60 is provided inside the resting surface 80 (FIGS. 5, 6) able to recognize the test tube container 5 just received by the resting surface 80. In fact, each test tube container 5 contains an RFID (transponder) identification device which communicates the identification data of container 5 to antenna 60; this is obviously used to communicate to the central control unit 7 which test tube container 5 is located at that moment on the resting surface 80 to be handled.

Each revolving plate 9 comprises a base 40 and a shaped profile 41 (FIG. 7) such as to define two different locations capable of accommodating a test tube container 5. It is a depositing location 42, i.e. the innermost location for each of the two plates 9 (referring to FIG. 1), and an outermost working location 43, accessible to each of the two test tube handling devices 3.

Each plate 9 can rotate by 180°, so that each of the two locations can alternatively be the depositing one 42 and the working one 43.

The rotation of plate 9 is made possible by the actuation of a motor 44 and by the motion transmission through a shaft 45 (FIG. 8); plate 9, in its rotational motion, does not lock in intermediate positions, thus alternating only between the extreme positions, i.e. 0° and 180°.

Figure 7:
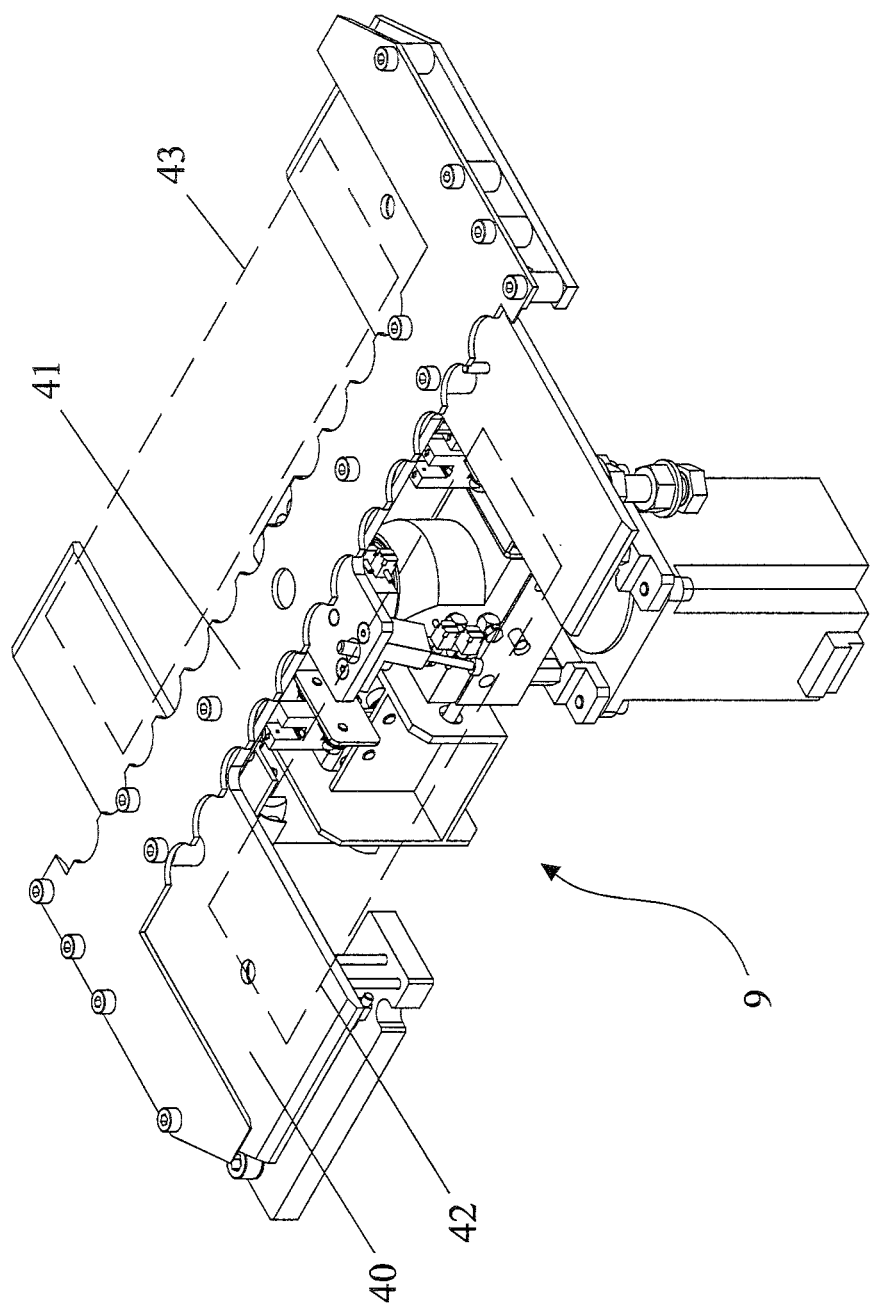
FIG. 7 shows a perspective view of a revolving plate.
Figure 8:
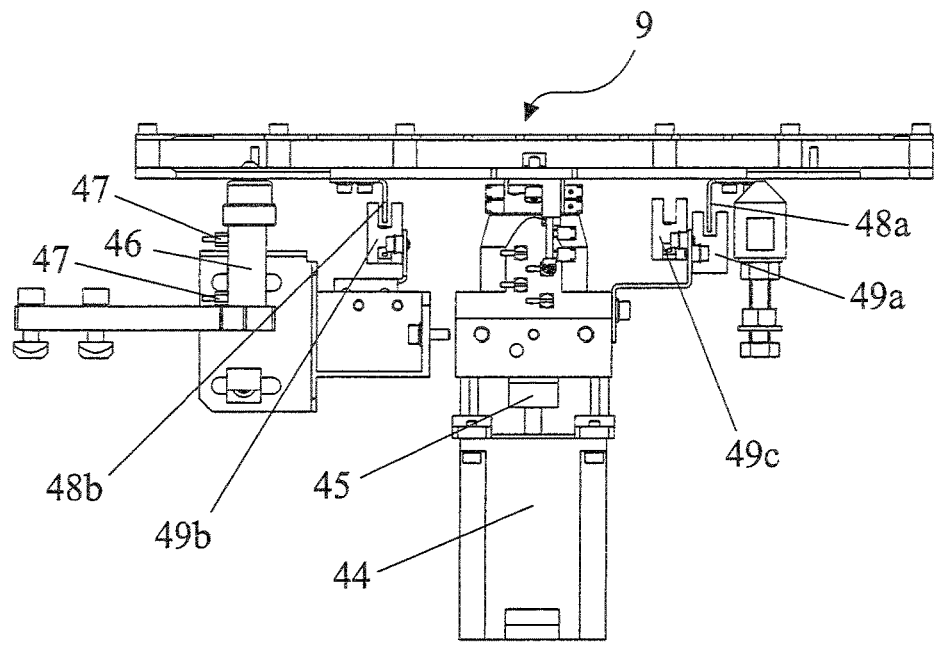
FIG. 8 shows a right side view of the revolving plate.

The lock of the revolving plate 9 in each of the two positions is ensured by the action of a plate lock cylinder 46 powered by solenoid valves through two flow regulators 47 (FIGS. 7, 8).

In particular, during the rotation of plate 9, means for detecting the position of plate 9 are activated, consisting of the two cams 48a and 48b and three sensors: a home sensor 49a, a 0° sensor 49b and a 180° sensor 49c (FIG. 8). In the situation in which plate 9 is at 0° (FIG. 8), cam 48a engages the home sensor 49a, while cam 48b engages the 0° sensor 49b; in the rotation step of plate 9, when cam 48b engages the 180° sensor 49c, the reaching of the 180° position by the plate is recognized and then the plate lock cylinder 46 is activated. Obviously, cylinder 46 acts in the same manner also upon the subsequent return of plate 9 to the 0° position.

Figure 9:
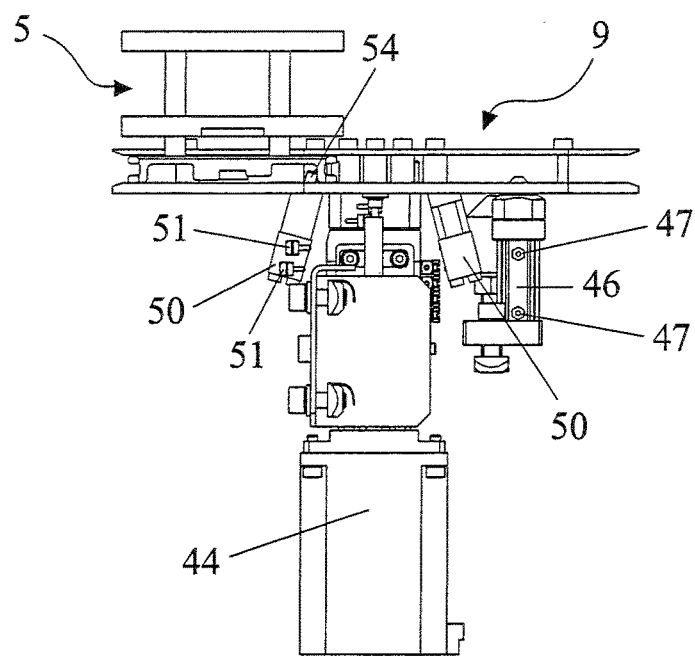
FIG. 9 shows a front view of the revolving plate.

Moreover, each plate 9 has two test tube container lock cylinders 50 (FIG. 9), each for each of the two locations of plate 9 capable of accommodating a test tube container 5. As usual, cylinders 50 are powered by solenoid valves through two flow regulators 51 and they contribute to the movement of a block 54 which holds the test tube container 5, if present on the revolving plate 9 (as shown in FIG. 9, in the left location of the plate).

Finally, a test tube unloading pipe 52 is also provided (FIG. 1) from which they end up in an unloading apparatus 53 with multiple racks, identical to that described in patent application MI2012A001111 by the Applicant.

The operation is as follows: the apparatus of the invention serves to interface the refrigerated store 1 and conveyor 4, enabling a dual operation, i.e. the loading of test tubes 2 from the refrigerated store 1 to conveyor 4 and the unloading of test tubes 2 from conveyor 4 to the refrigerated store 1.

Assuming that tubes 2 travel along conveyor 4 from the right leftwards (as depicted in FIG. 1), the central control unit 7 provides to suitably divert carriers 200 along a first or a second secondary lane of conveyor 4, so that they interface with the first or the second of the two test tube handling devices 3, depending on the temporary loading or unloading requirements of test tubes 2.

In the embodiment shown in FIG. 1, the test tube handling device 3 on the right is intended to load test tubes 2 from the refrigerated store 1 to conveyor 4; accordingly, only empty carriers 200 ready to accommodate test tubes 2 recovered from store 1 are diverted at the interface therewith. Conversely, the test tube handling device 3 on the left carries out the unloading of test tubes 2 from conveyor 4 to the refrigerated store 1, therefore in the corresponding secondary lane, carriers 200 with test tubes 2 are accommodated which are ready to be picked up and then stored in the refrigerated store 1.

Both in the loading and in the unloading area, at the end of the interfacing by the test tube handling device 3 with each handling device 200, the latter is released (filled with a test tube 2 in the loading area, deprived of a test tube 2 in the unloading area) and returns along the main lane of conveyor 4.

Let's now concentrate on the operation of loading test tubes 2 from store 1 to conveyor 4: it may be necessary if a test tube 2, previously stored in the refrigerated store 1, needs to be recovered along conveyor 4 to be directed to a specific testing module, for example to replicate some tests whose results are deemed abnormal or unsatisfactory, or simply for the purpose of checking and validating the previous results.

The test tube must be picked up from one of the test tube containers 5 stored in store 1. The rack handling mechanism inside store 1 itself allows the rack containing the concerned test tube container 5 to position itself at such a height that the translation of the test tube container 5 is perfectly horizontal. At the same time, the container handling device 8 moves longitudinally, positioning itself in the vicinity of the appropriate lane, ready to accommodate container 5 that is going to be ejected. The sliding of the handling device 8 takes place thanks to the electrical motor 162 (FIG. 11) which drives belt 161 connected to the sliding guide 16 along which carriage 160 slides, integral to the container handling device 8.

At this point, the sliding door opening cylinder is activated, the cylinder comprising the slider 11 (FIGS. 5, 6) the upwards translational motion of which is controlled: thereby, tongue 13 engages appendix 110 and therefore the sliding door 10 is raised (FIG. 12, although it already shows the test tube container 5 accommodated by device 8, whereas the step in which container 5 is still inside the refrigerated store 1 is now being described).

The container handling device 8, before accommodating the test tube container 5, is in a configuration in which both the front block 81 and the resting surface 80 are in the rest position, i.e. "low" (FIG. 1).

The actuation of the pneumatic cylinder 29 (according to what is already known from patent EP-2240787) allows the horizontal sliding of the front block 81, which penetrates inside the raised sliding door 10. Afterwards, the raising is controlled to the "high" position of both the front block 81 and of the resting surface 80, to ensure that the subsequent translation of the test tube container 5 is perfectly horizontal. Such a raising takes place by the action of the pneumatic cylinders 27 (for the front block 81) and 31 (for the resting surface 80), respectively, and can be seen in FIG. 14 (by comparison with FIG. 13) observing the corresponding pistons 270 and 310 of the two cylinders 27 and 31.

Figure 14:
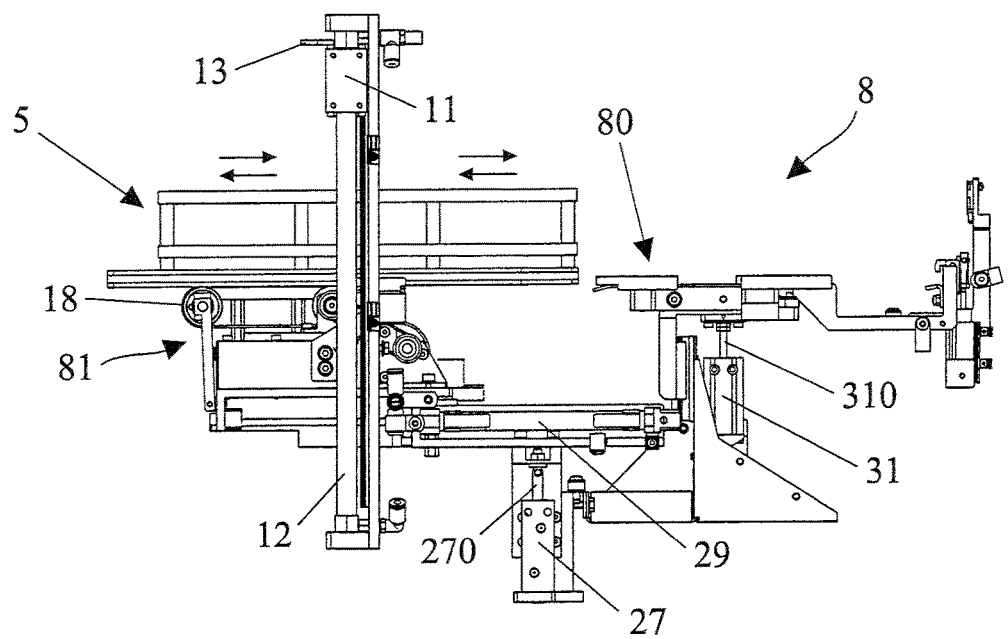
Figure 15:
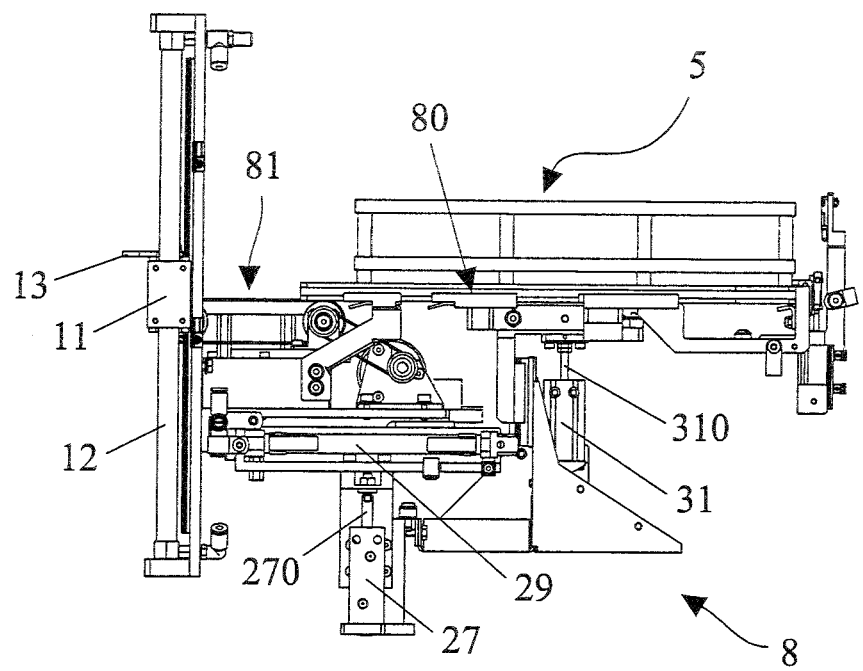
Figure 16:
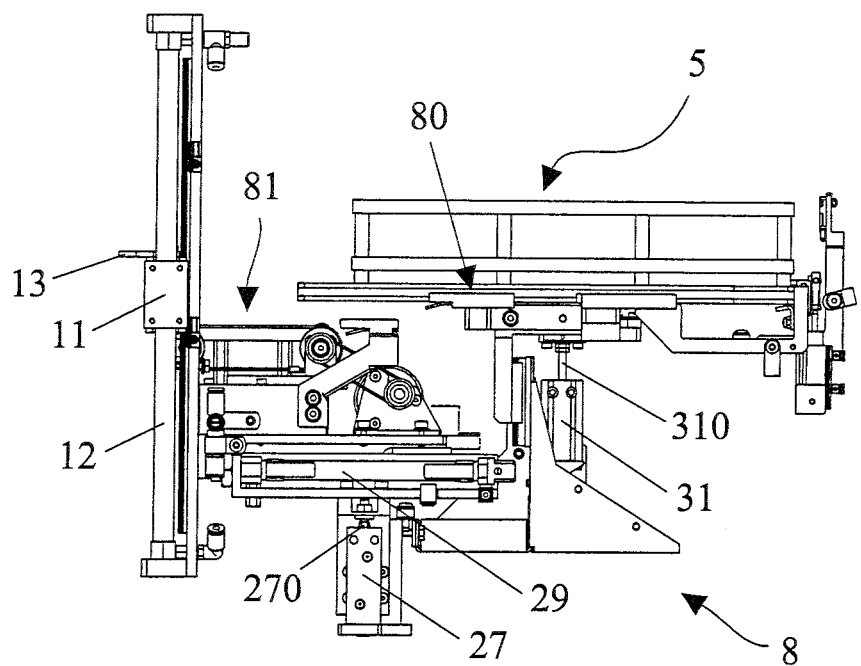

At this point, the actual displacement of the test tube container 5 from within the refrigerated store 1, i.e. from one of its racks, towards the container handling device 8, may take place; a first step of this displacement is favored by the action of the toothed translation track 18 which draws the test tube container 5 to the right (as shown in FIG. 14), which then combines with the approach of the front block 81 to the resting surface 80, again thanks to the action of the pneumatic cylinder 29. Thereby, the transfer of the test tube container 5 on the resting surface 80 of the container handling device 8 is completed (FIG. 15), and the sliding door 10 of store which had previously been raised can therefore be closed (by lowering slider 11). Afterwards, the pneumatic cylinder 27, and thus the whole front block 81, is lowered so as to make the handling device 8 take on a "low-high" configuration (FIG. 16).

In such a configuration, the container handling device 8, including at this point container 5 suitably detected by antenna 60 as well as locked by hook 35, then travels parallel to conveyor 4 towards the loading revolving plate 9.

Figure 17:
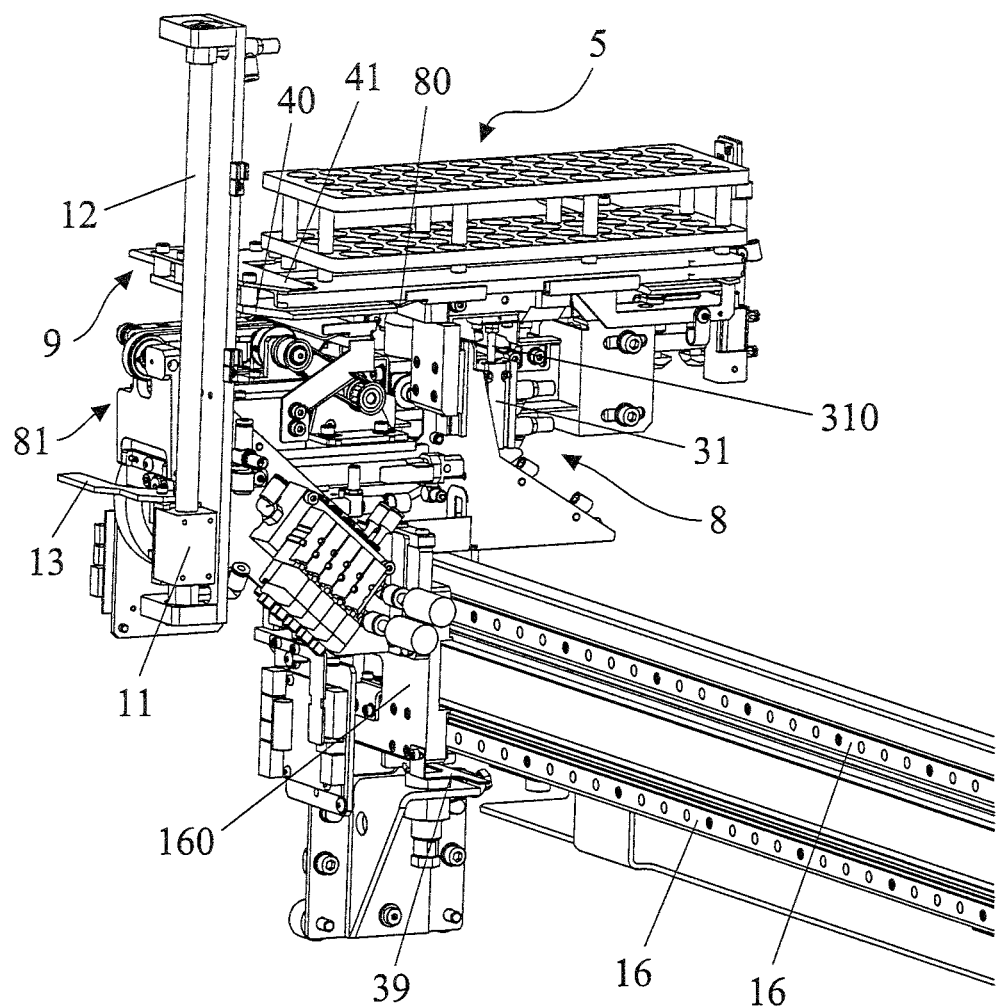
FIGS. 17, 18 and 19 show perspective views of three different steps of the interaction between the container handling device and one of the revolving plates.

When it arrives in the vicinity of the plate itself, the front block 81 of the container handling device 8, precisely because it has previously been lowered, is inserted in a position below base 40 of plate 9 (FIG. 17).

Figure 18:
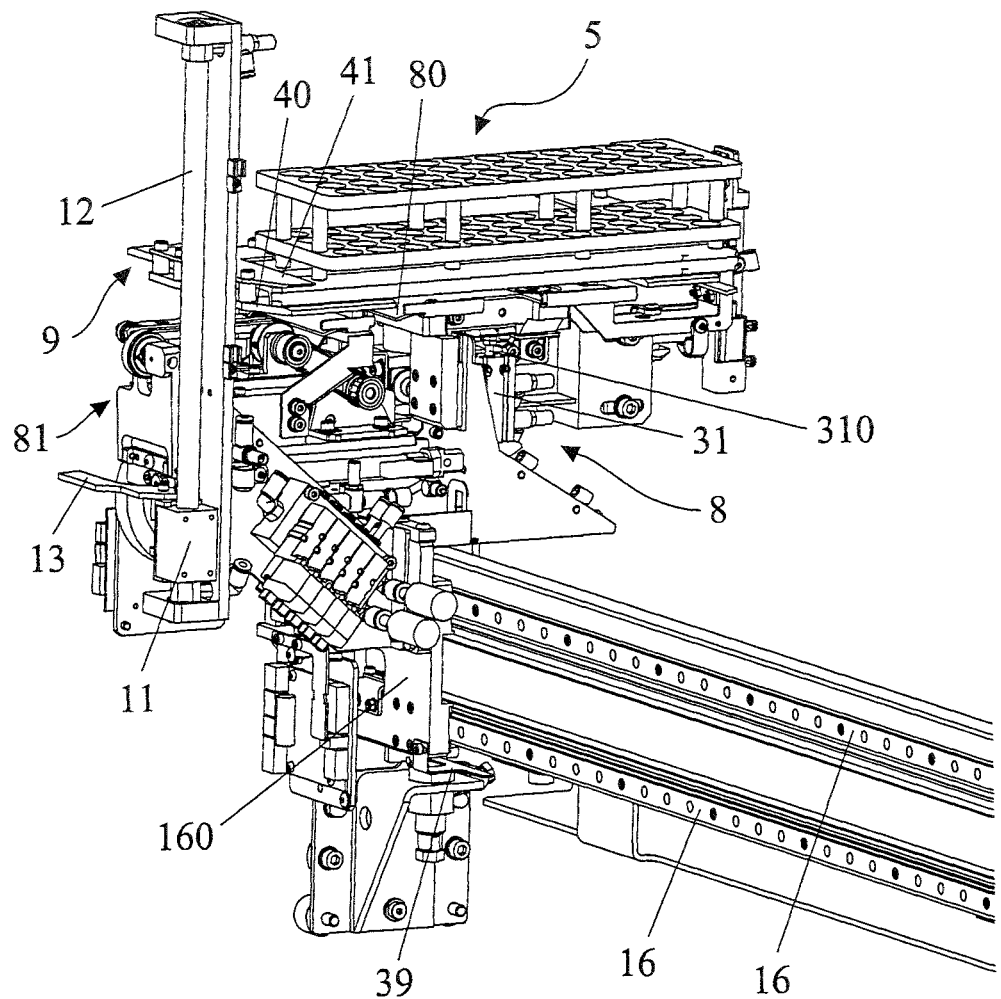

Simultaneously, the hollow central region of the depositing location 42 of plate 9 (FIG. 7) receives the test tube container 5 handled by the handling device 8. Thereafter, the action of the pneumatic cylinder 31 also facilitates the lowering of the resting surface 80 of the container handling device 8: this allows the test tube container 5 to lay onto base 40 of plate 9 (FIG. 18).

Figure 19:
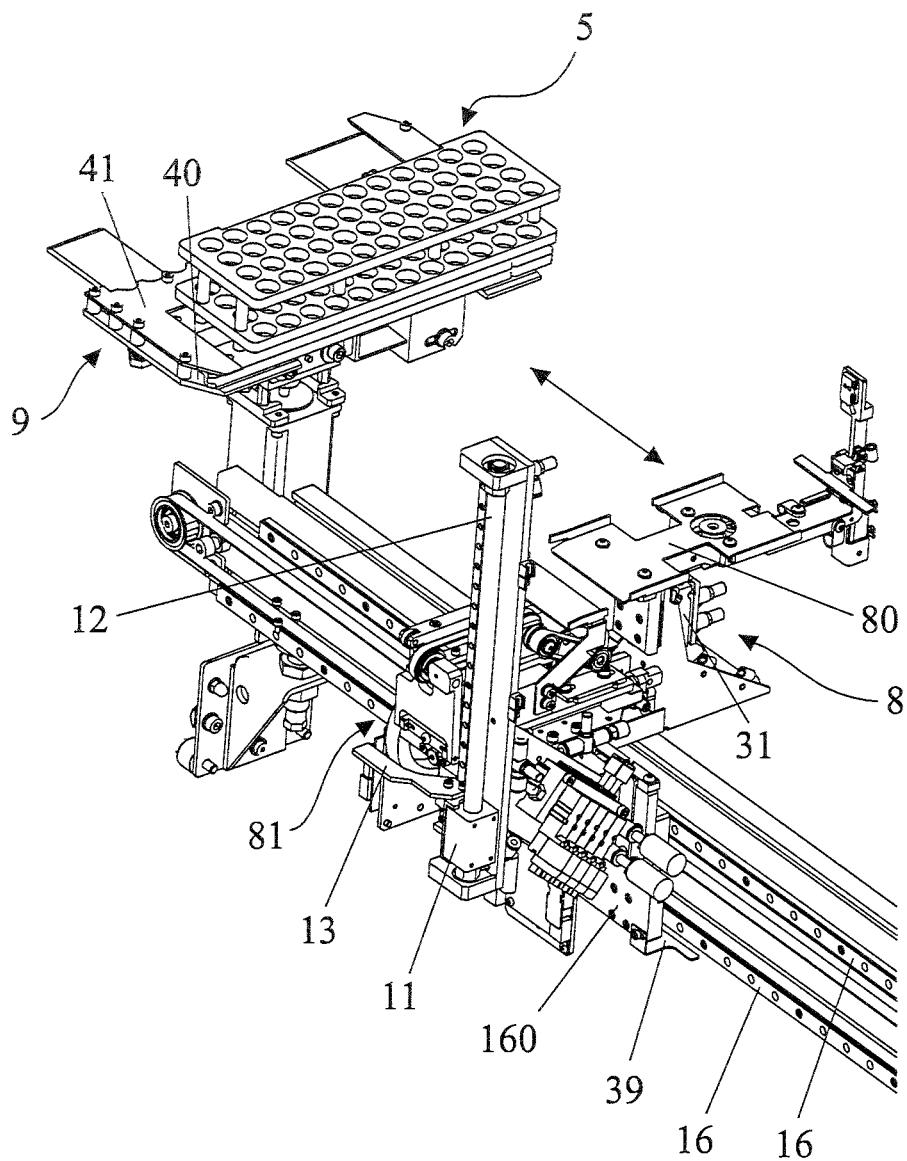

The container handling device 8, which is empty at this point and has both the front block 81 and the resting surface 80 in "low" position (thus returning to the rest configuration in FIG. 13), moves back to a position advantageously more or less distant from both plates 9 (FIG. 19).

The test tube container 5 just received is meanwhile locked on plate 9 thanks to the exit of block 54 (FIG. 9), controlled by the test tube container lock cylinder 50; also plate 9 is in turn locked by the plate lock cylinder 46 (FIGS. 8, 9), in the position corresponding to 0°.

After a few moments, the lock imposed by cylinder 46 is deactivated and thus plate 9 rotates by 180°: thereby, the test tube container 5 substantially moves from the depositing location 42 to the outermost working location 43. At this point, subsequent to a new activation of the lock cylinder 46 and thus to a new locking of plate 9, the test tube handling device 3 can go to pick up the desired test tube 2, in any position it is within the test tube container 5 and according to the instructions from central control unit 7. This is because, as said, the test tube handling device 3 (FIG. 2) comprises a mechanical arm 71 capable of moving along the three axes x, y, z, reaching all the positions where a test tube 2 can be inside the test tube container 5 positioned in the working location 43 of plate 9 (FIG. 1).

The test tube 2 picked up by clamp 72 of the test tube handling device 3 is then loaded onto the handling device 200 in stand-by, empty, along the secondary lane of conveyor 4. Alternatively, if the test tube 2 needs not be redirected to a testing module but simply discarded because the life time of the relevant specimen has ended, it is directed into the test tube unloading pipe 52 to end up in the unloading apparatus 53 with multiple racks (FIG. 1).

The subsequent rotation of plate 9 returns the test tube container 5 to the depositing location 42, from which the container handling device 8 can pick it up again (after having taken back the configuration in FIG. 16, i.e. after the raising of the resting surface 80 from the "low" to the "high" position) and return it inside the refrigerated store 1, on the same rack and along the same lane already occupied before. The movement of the mechanical elements referred to this step of reinsertion of the test tube container in the refrigerated store 1 is the same as previously described in relation to the opposite operation of picking up the test tube container 5 from store 1, although now they obviously occur in the reverse order. For this reason, for example, the arrows in FIG. 14 indicating the displacement of the test tube container 5 are bidirectional.

The situation described has shown the path of a single test tube container 5 on plate 9. Obviously, once a test tube container 5 has been laid on plate 9, and following the rotation of plate 9 itself, container 5 moves from the depositing location 42 to the working location 43, plate 9 can immediately receive in the depositing location 42 now empty a second test tube container 5, again handled by the container handling device 8, and which therefore occupies plate 9 together with the previous one. This situation occurs, for example, when it is necessary to recover two test tubes in a short time, on conveyor 4, which are stored in the refrigerated store 1 in different test tube containers 5, which are located on racks and/or lanes very distant from one another.

The apparatus behaves in a totally similar manner in the case of the unloading operation of test tubes 2 from conveyor 4 to store 1. The discussion is therefore identical, obviously considering the mirror-like arrangement of the unloading plate 9 and of the corresponding test tube handling device 3, as well as the fact that the test tubes 2 in this case follow the opposite path, i.e. they are picked up from the handling device 200 on conveyor 4 and positioned in the test tube container 5 present in the working location 43 of the revolving plate 9.

In the practice, it has been found that the apparatus thus described can achieve the intended objects ensuring, thanks to the use of two distinct test tube handling devices 3 (each coupled to a revolving plate 9), the possibility to carry out, also possibly simultaneously, the operations of loading test tubes 2 from a refrigerated store 1 to a conveyor 4 and vice versa unloading test tubes 2 from conveyor 4 to the refrigerated store 1.

In fact, according to the operational requirements that may occur at any moment, the container handling device 8 is appropriately directed towards one or the other of the two revolving plates 9, therefore moving the test tube containers 5 as appropriate and carrying out the related operations of loading or unloading with a certainly greater frequency compared to known solutions, such as that described in the previous patent EP-2240787 by the Applicant: in fact, both in the case of loading and of unloading, a single three-axis robot is used therein to handle the test tubes, which robot can move from one end to the other of the apparatus, and thus inevitably the handling frequency of the test tubes is lower and times are longer.

The solution of the present invention therefore allows coping with the needs of a quicker storage or release of specimens into/from the refrigerated store 1, in response to the ever increasing operating volumes of a laboratory automation system in terms of number of biological specimens involved.

Several changes and variations may be made to the invention thus conceived, all falling within the scope of the inventive concept.

In the practice, the materials used as well as shapes and sizes, may be any, according to the requirements.

The invention claimed is:

1. An apparatus for automatically depositing, storing and recovering specimens of biological material, contained in test tubes, in/from a refrigerated store in which test tubes are stored in containers of a plurality of test tubes,
   wherein it comprises
   two test tube handling devices suitable for handling single test tubes, each attached to a respective support bracket at the opposite ends or the refrigerated store, and for loading/unloading single test tubes to/from carriers of single test tubes movable on a conveyor adjacent to the refrigerated store,
   two revolving plates, in correspondence with each of said two test tube handling devices, each one comprising only two different locations, a depositing location and a working location each able to accommodate a container of a plurality of test tubes, a rotation of 180° transforming the depositing location into a working location and vice-versa, thus letting the revolving plate alternate only between two extreme positions,
   a container handling device configured for horizontally loading the containers from the refrigerated store and supply them to the depositing location of one of said two revolving plates and vice-versa, said container handling device being horizontally movable along a sliding guide mounted on a profile adjacent to the refrigerated store such that said container handling device can reach different positions of said refrigerated store, and a control unit coordinating the activities of said devices for handling the test tubes and containers and of each of said revolving plates during the loading/unloading operations.

2. The apparatus according to claim 1, wherein said revolving plate comprises a plate lock cylinder to lock said plate in said positions, means for detecting the position of said plate comprising two cams capable of alternatively engaging three sensors, and furthermore two test tube lock cylinders for each of the two locations of said revolving plate.

3. The apparatus according to claim 1, wherein said container handling device comprises a front block on which said container of a plurality of test tubes slides translating from said refrigerated store to a resting surface on said container handling device and vice-versa, both said front block and said resting surface being vertically mobile independently of each other between a low position and a high position.

4. The apparatus according to claim 3, wherein said container handling device comprises a sliding door opening cylinder consisting of a slider sliding along a rod, said slider being hooked to a tongue capable of hooking to an appendix positioned in correspondence with each of the sliding doors of said store so as to raise said appendix and said sliding door.

5. The apparatus according to claim 4, wherein said container handling device comprises a test tube container lock cylinder actuated by a test tube container presence sensor on said resting surface, and an antenna for recognizing said container of a plurality of test tubes present on said resting surface.

\* \* \* \* \*